United States Patent [19]

Hubbard et al.

[11] Patent Number: 5,190,521
[45] Date of Patent: Mar. 2, 1993

[54] APPARATUS AND METHOD FOR RAISING A SKIN WHEAL AND ANESTHETIZING SKIN

[75] Inventors: Vance M. Hubbard; Welton K. Brunson, both of Bedford; V. C. Saied, Wichita Falls, all of Tex.

[73] Assignee: Tecnol Medical Products, Inc., N. Richland Hills, Tex.

[21] Appl. No.: 572,508

[22] Filed: Aug. 22, 1990

[51] Int. Cl.[5] .................... A61M 31/00; A61M 5/24
[52] U.S. Cl. .................................. 604/51; 604/117; 604/206
[58] Field of Search .............. 604/112, 117, 192, 199, 604/201, 204, 206, 212, 240, 241, 243, 905, 51; 206/363–366, 368

[56] References Cited

U.S. PATENT DOCUMENTS

| 2,696,212 | 12/1954 | Dunmire | 604/199 X |
| 3,270,743 | 9/1966 | Gingras | 604/199 X |
| 3,380,450 | 4/1968 | Adelberger | 604/117 |
| 3,512,524 | 5/1970 | Drewe | 604/206 X |
| 3,783,876 | 1/1974 | Dye | 604/117 |
| 3,967,621 | 7/1976 | Schwarz | 604/206 X |
| 3,995,629 | 12/1976 | Patel | 604/117 |
| 4,758,230 | 7/1988 | Rycroft | 604/206 X |
| 4,799,926 | 1/1989 | Haber | 604/187 |

*Primary Examiner*—John D. Yasko
*Assistant Examiner*—Adam J. Cermak
*Attorney, Agent, or Firm*—Baker & Botts

[57] ABSTRACT

The sight of a large I.V. needle makes one shiver with fright due to one's association of an I.V. needle with pain. An apparatus and method for anesthetizing the intended site for I.V. needle insertion is provided to reduce or eliminate the pain. The apparatus (10) comprises a storage chamber (12) containing an anesthetizing agent (22) and coupled to a seat member (14). The seat member (14) further holds a needle (16) in place and pierces the storage chamber (12). Alternate embodiments of the apparatus (10) include a seat member (46,56) which allows the needle (52,68) to penetrate the storage chamber (40,62) just prior to use. The apparatus pierces the skin, injects the anesthetizing agent and induces a skin wheal at the intended site.

12 Claims, 5 Drawing Sheets

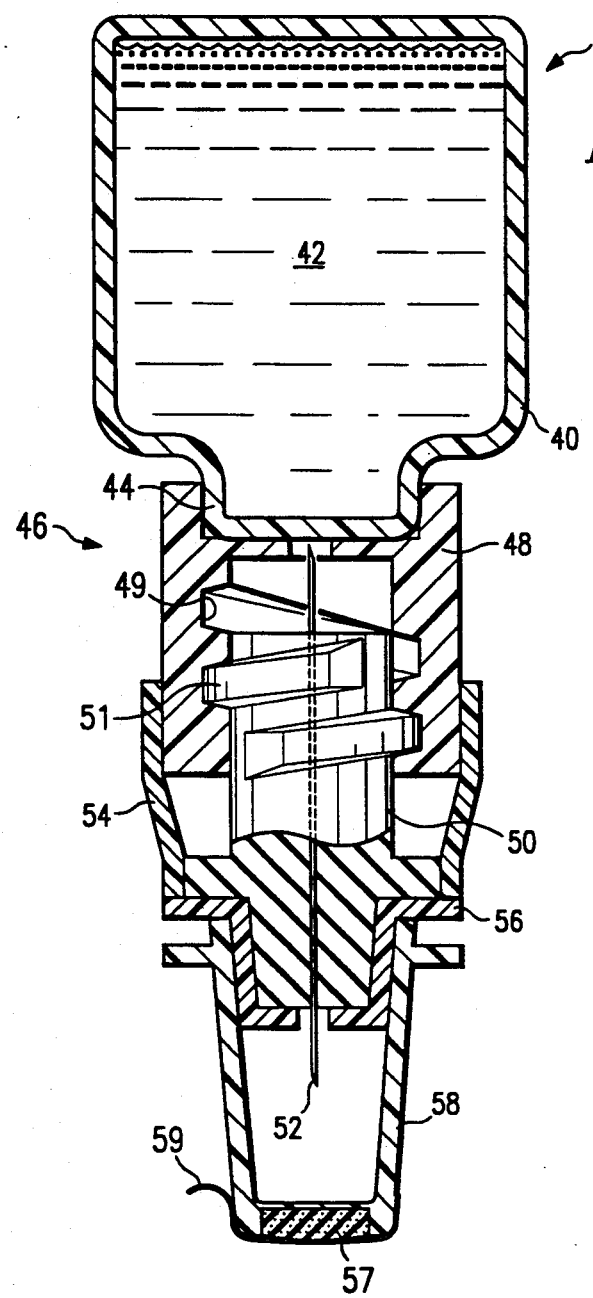
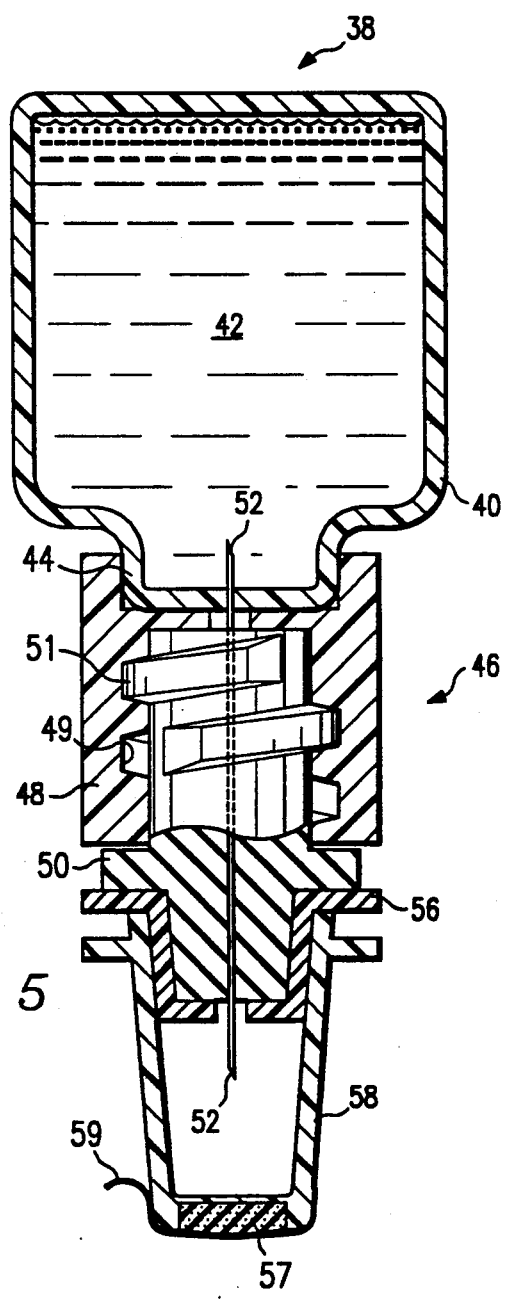
FIG. 4
FIG. 5

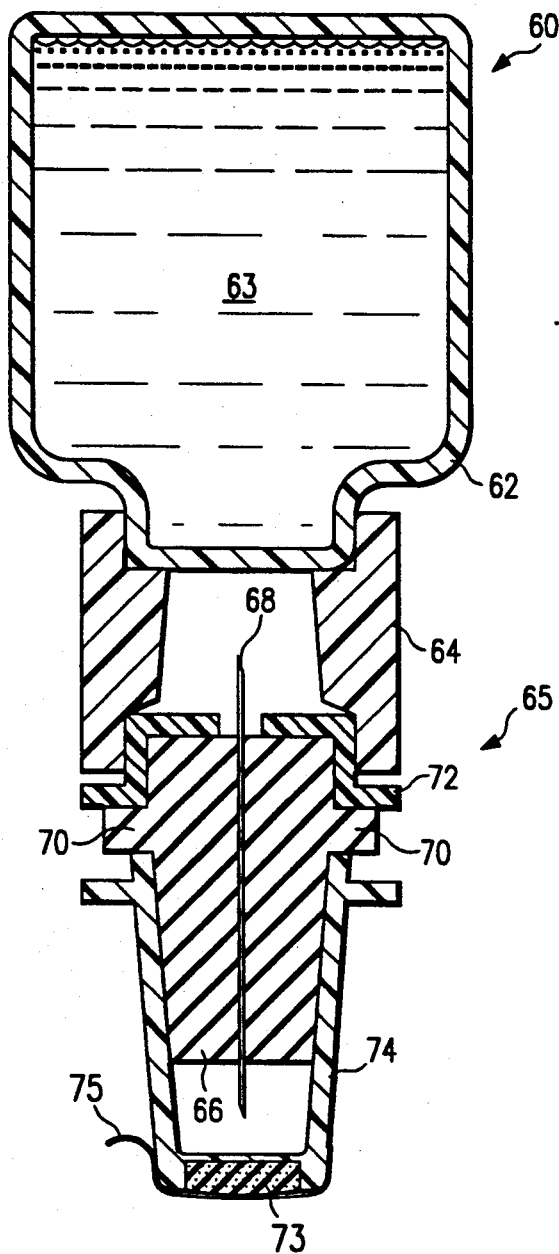
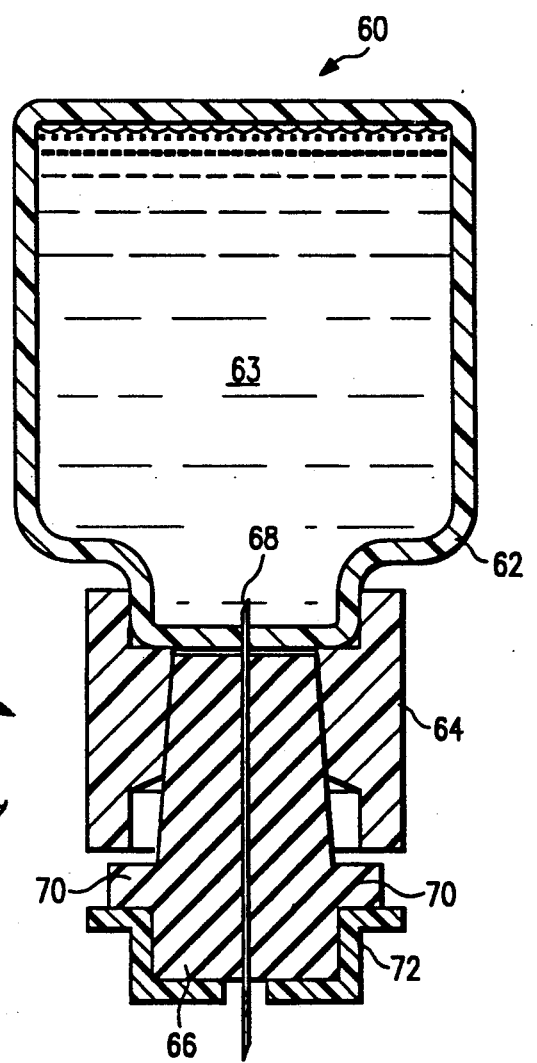
FIG. 6
FIG. 7

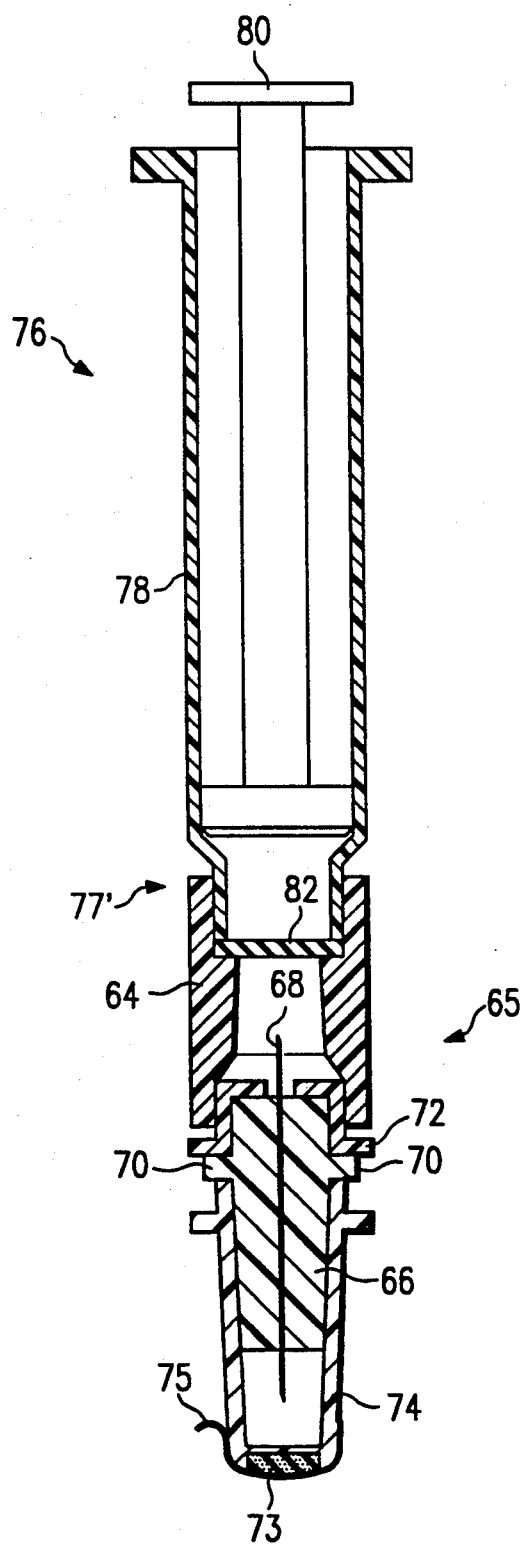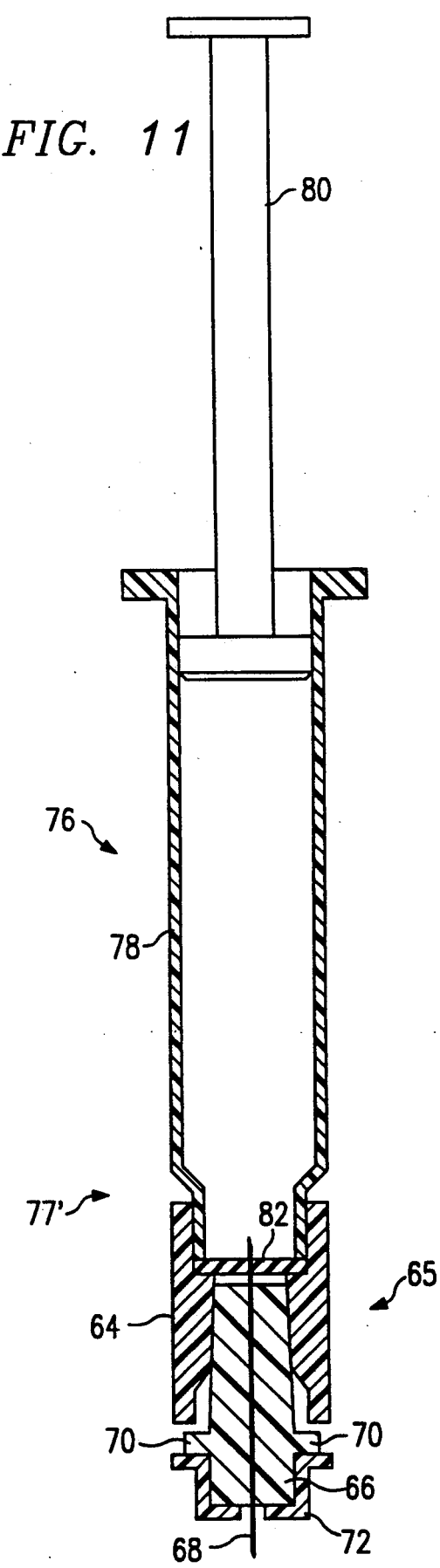

APPARATUS AND METHOD FOR RAISING A SKIN WHEAL AND ANESTHETIZING SKIN

TECHNICAL FIELD OF THE INVENTION

This invention relates in general to medical products, and more particularly to an apparatus and a method for anesthetizing skin.

BACKGROUND OF THE INVENTION

The insertion of an intravenous (I.V.) catheter can be a frightening and painful experience. The sight alone of the large gauge needle typically used in an I.V. catheter is enough to cause the patient to become anxious and tense. The patient's react to become tense and hard, making needle penetration difficult and painful.

Typically, the I.V. needle must be inserted into a vein along the forearm or on the back of a hand. It is not uncommon for a first attempt to insert the I.V. needle to fail because it is difficult to locate a vein in some patients. As a result, further painful probing is required to locate the vein and to insert the I.V. needle.

After insertion, an I.V. catheter may remain in place for an extended period of time. The site of penetration may remain painful due to the pulling and stretching of the catheter. As a result, the patient is subjected to pain and suffering repeatedly and needlessly.

Accordingly, a need has arisen to provide an apparatus to numb the intended I.V. needle penetration site in order to lessen the pain and suffering usually associated with I.V. catheter insertions. The present invention anesthetizes the general area around the needle penetration site and induces a wheal for ease of I.V. insertion. The present invention is further directed to overcoming one or more of the problems as set forth above.

SUMMARY OF THE INVENTION

In accordance with the present invention, an apparatus and method for anesthetizing skin is provided which substantially eliminates or reduces pain introduced by I.V. catheter administration.

In one aspect of the present invention, an apparatus for anesthetizing skin is provided. The apparatus comprises a storage chamber for containing an anesthetizing agent, means for injecting the anesthetizing agent into the skin and a spacing element for determining the depth of injecting means penetration into the skin.

In another aspect of the present invention, an apparatus for anesthetizing skin prior to an I.V. needle insertion is provided. The apparatus comprises a storage chamber for containing an anesthetizing agent and a seat member coupled to the storage chamber at one end. It further comprises a needle arranged for piercing the storage chamber wall and acquiring the anesthetizing agent. To vary the amount of needle penetration, a detachable spacer is coupled to the seat member. There is also provided a cap detachably coupled to the apparatus for shielding the needle from contaminants.

In yet another aspect of the present invention, there is provided a method for anesthetizing skin comprising the steps of first pinching a section of skin to be anesthetized, then pricking the section of skin with an injector containing an anesthetizing agent to form a skin wheal so that it is readily accessible for intravenous injections or the like.

BRIEF DESCRIPTION OF THE DRAWING

The foregoing, and additional objects and advantages of the invention will become more apparent as the following detailed description is read in conjunction with the accompanying drawing wherein like reference characters denote like parts in all views and wherein:

FIG. 4 is a cross-sectional view of another embodiment of apparatus that is constructed in accordance with the invention;

FIG. 5 is a view similar to FIG. 4, but showing the apparatus as it is ready for use;

FIG. 6 is a cross-sectional view of still another embodiment of the invention that is also constructed in accordance with the invention;

FIG. 7 is a view similar to FIG. 6 showing the apparatus of FIG. 6 as it is ready for use;

FIG. 10 is a cross-sectional view of a modification of the apparatus of FIG. 6 that is also constructed in accordance with the invention; and FIG. 11 is a view similar to FIG. 10 showing the apparatus of FIG. 10 as it is ready for use.

DETAILED DESCRIPTION OF THE INVENTION

Figure 1:
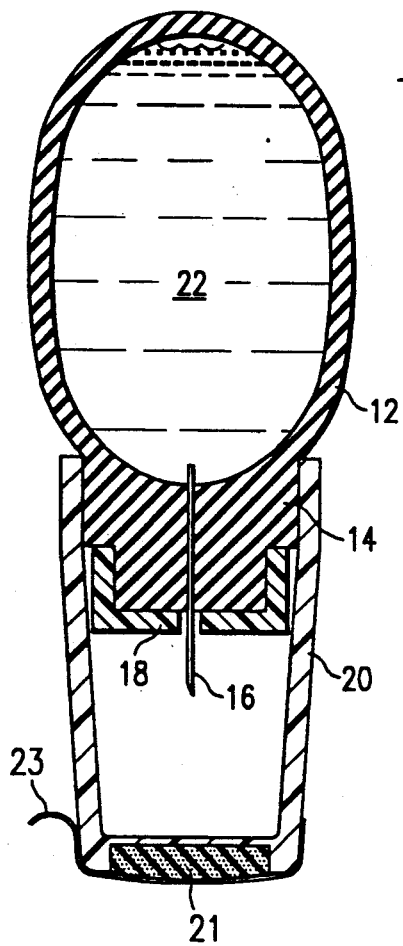
FIG. 1 is a cross-sectional view of apparatus constructed in accordance with the present invention.
Figure 2:
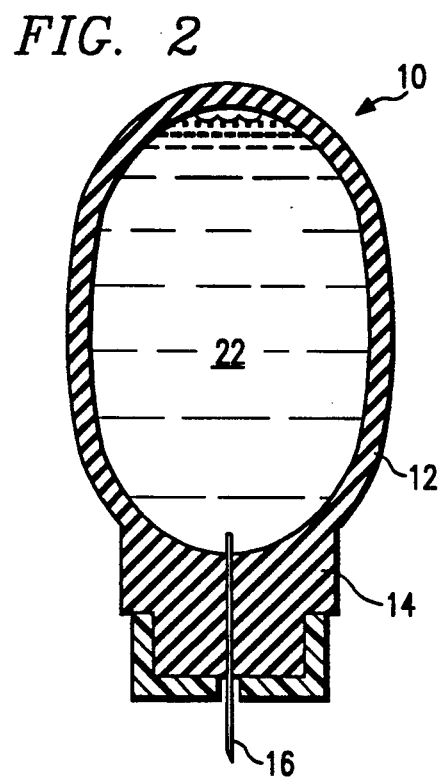
FIG. 2 is a view similar to FIG. 1, but showing the apparatus of FIG. 1 when it is ready for use.

With reference to the drawings, FIG. 1 and FIG. 2 show an embodiment of an apparatus for anesthetizing skin constructed in accordance with the teaching of the present invention. The apparatus, indicated generally at 10, is shown in storage prior to use in FIG. 1 and ready for use in FIG. 2.

The apparatus 10 comprises a storage chamber 12. The storage chamber 12 may be made of a pliable and flexible material such as rubber, plastic and the like so that the wall of the storage chamber 12 may be depressed to decrease the volume thereof. One end of the storage chamber 12 is fixedly attached to a seat member 14 made of a rigid material such as rubber, plastic and the like. The rigid seat member 14 further accommodates a needle 16 located along its longitudinal axis and maintains a fixed spatial relationship between the storage chamber 12 and the needle 16. The needle 16 is hollow to allow the passage of fluids and extends beyond the seat member 14 for inflicting a slight skin penetration. In the present embodiment of the instant invention, the needle 16 is shown penetrating the storage chamber 12 through the chamber wall even prior to use. It preferable that the needle 16 is of a small size, such as 30 gauge, so that it does not conduct the fluid contained in the storage chamber 12 unless the fluid is forced out by applying pressure to the chamber wall. The small needle size is also preferable because its insertion into the skin is slight and painless.

The human body experiences physiological changes as it matures. One of the changes in the skin is the thinning of the various tissue layers. In order to accommodate the difference in skin thickness among the young, the elderly and those in between, a spacer 18 is provided to vary the depth of needle penetration into the skin. The spacer 18 is coupled to the seat member 14 to decrease the length of the needle 16 available for skin penetration. To increase the depth of penetration, the spacer 18 may be removed to expose more length of the needle 16. The spacer 18 may be made of similar material as the seat member 14 and may be either rigid or slightly flexible.

The apparatus 10 further includes a cap 20 detachably secured over the needle 16. The cap shields the needle 16 from contaminants in the environment and keeps it sterile until the apparatus 10 is ready to be used. The cap 20 may be made of materials such as plastic.

Additionally, an antiseptic applicator 21 may be coupled to the tip of the cap 20. The preferred embodiment of the applicator 21 is in the form of a sponge substantially saturated with an antiseptic solution, and securely mounted within a cavity located at the tip of the cap 20. A strip of foil 23 substantially covers and seals the applicator 21 to prevent contamination and evaporation of the antiseptic solution. The foil 23 includes a portion which is graspable in order to facilitate tearing and removing the foil 23 from the antiseptic applicator 21 to expose the sponge. The antiseptic solution is applied to a site on the skin intended for I.V. penetration by rubbing the sponge there.

The storage chamber 12 contains an anesthetizing agent 22 which may be of various compositions. Examples of the anesthetizing agent 22 are saline solutions and medicated saline solutions. It may be appreciated that in an alternate application, the storage chamber 12 may be filled with other types of solutions such as allergy inducing compounds which are then introduced by the needle 16 into a patient in an allergy test.

FIG. 2 illustrates the apparatus 10 ready to be used. The cap 20 has been removed to expose the needle 16 and the seat member 14. The spacer 18 is shown attached to the seat member 14 in this instance, but may be removed if circumstances so dictate.

Figure 3:
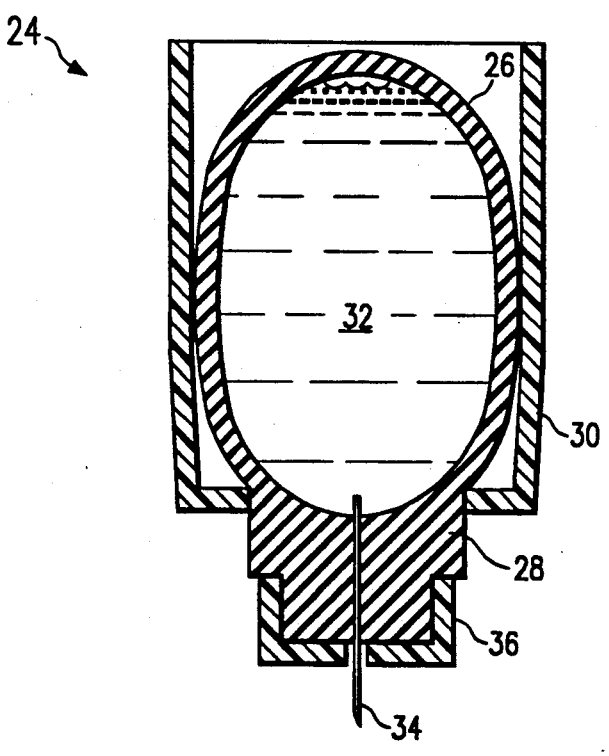
FIG. 3 is a cross-sectional view of a modification of the apparatus of FIG. 1 that is also constructed in accordance with the invention.

Referring to FIG. 3, a modification of the apparatus 10 is shown. The apparatus, indicated generally at 24, is constructed substantially similarly to apparatus 10 except for differences described in detail below. A storage chamber 26 is coupled to a seat member 28 at one end. A housing 30 surrounds the storage chamber 26 and is also attached to the seat member 28 at the same end. The housing 30 has an opening at the top to allow the entry of a finger or thumb to exert pressure on the storage chamber 26 during use. The housing 30 forms a substantially rigid shield around the storage chamber 26 to discourage discharge of the anesthetizing agent 32 through the needle 34 prior to usage. The seat member 28 and the housing 30 may or may not be of integral construction and the material thereof may or may not be alike. A spacer 36 may be further provided for determining the depth of penetration for the same purposes as enumerated above. A cap 20 and an antiseptic applicator 21 such as shown in FIG. 1 may also be included.

FIG. 4 and 5 show another embodiment of the present invention. The apparatus, indicated generally at 38, includes a storage chamber 40 for containing an anesthetizing agent 42. The storage chamber 40 is shown constructed in a generally rectangular shape with a protruding portion 44. It can be appreciated that the shape of the storage chamber 40 is not of great importance as long as the shape thereof facilitates the use of the apparatus 38 in accordance with the teaching of the present invention. The protruding portion 44 secures the storage chamber 40 to a seat member 46.

Seat member 46 comprises a first and second portion 48,50. The first portion 48 is substantially tubular with a cavity extending from one end of the first portion to the other end. A needle 52 is firmly implanted within the second portion 50, with both ends extending beyond the second portion 50, and with one end extending into the cavity of the first portion 48. Thus the needle 52, arranged in this fashion, is poised for penetration into the storage chamber 40. The needle 52 may be made to pierce the storage chamber 40 by manipulating the first and second portions 48,50 of the seat member 46.

The first and second portions 48,50 are coupled together by a twist-lock mechanism as known in the art of coupling mechanisms. The second portion 50, at a first position, is partially contained within the cavity of the first portion 48 and is engaged by interlocking fingers to the first portion 48. By twisting the second portion 50 with respect to the first portion 48, the second portion 50 is advanced further into the first portion cavity to a second position, as shown in FIG. 5. The twist-lock arrangement additionally allows the needle 52 to move from a first position apart from the storage chamber 40 to a second position, where it penetrates the storage chamber 40 walls and reaches the anesthetizing agent 42 contained therein.

It can be appreciated that the twist-lock mechanism of the instant embodiment may be substituted by alternate coupling mechanisms and/or devices which perform substantially the same function to achieve substantially the same result. For example, the first and second portions 48,50 may be coupled by mating screw threads where the second portion 50 may be rotatably advanced to the second position; the second portion may held in the first position by stop tabs, and the second portion may be advanced to the second position by forcibly pressing it into the first portion and breaking the stop tabs.

The second portion 50 and part of the first portion 48 of the seat member 46 are preferably encased in a casing 54, which securely holds the second portion 50 in the first position and prevents the needle 52 from penetrating the storage chamber 40 prematurely. The casing 54 is removed prior to use. A spacer 56 is attachable to the second portion 50 and determines the penetration depth of the needle desired for the same reasons enumerated above. A detailed discussion of the spacer 58 may be found in association with FIG. 1.

Further provided is a cap 58 which is attachable to the spacer element 56. The cap 58 shields the needle 52 from the environment and keeps it sterile. An antiseptic applicator 57 is also provided, which includes a sponge saturated with an antiseptic solution and a protective foil 59, such as described above.

As shown in FIG. 5, the apparatus 38 is ready for use. The second portion 50 has been advanced from the first position to the second position by twisting the second portion 50 with respect to the first portion 48. As the second portion 50 advances to the second position, the needle 52 approaches the storage chamber 40 and eventually pierces it. Once the twist-lock mechanism locks the second portion in the second position, as shown in FIG. 5, the cap 56 may be removed, and the apparatus is ready to be used for anesthetizing the general area intended for I.V. needle insertion. The apparatus 38 is shown with the spacer 58 in place.

Referring now to FIG. 6, a third embodiment of the present invention is shown. The apparatus, indicated generally at 60, comprises a storage chamber 62 made of a flexible and pliable material and contains a solution 63. The storage chamber 62 is coupled to a first portion 64 of a seat member 65 which is generally tubular in shape. The first portion 64 of the seat member 65 has a first recess at one end for coupling to the storage chamber 62 and a second recess at the other end for coupling to a second portion 66.

The second portion 66 is detachable from the first portion 64 of the seat member 65 and holds a needle 68 substantially along the longitudinal axis of the apparatus 60 and extends at both ends beyond the boundaries of the second portion 66. The second portion 66 includes a stop 70 protruding generally perpendicularly from the longitudinal line of the apparatus 60 and serves as a stop to control the length of the second portion 66 which may enter the cavity of the first portion 64. The stop 70 essentially divides the second portion 66 into two unequal sections, where the distance from one end to the stop 70 is longer than the distance from the other end.

The apparatus 60 further includes a spacer 72 detachably coupled to the shorter end of the second portion 66. As shown in FIG. 6, when the apparatus 60 is in storage, the shorter section of the second portion 66 is coupled to the first portion 64 along with the spacer 72 located therebetween. Arranged in this manner, the needle 68 is substantially spaced from the storage chamber 62. A cap 74 is coupled to the second portion 66 and over the needle 68 to keep it sterile. An antiseptic applicator 73 is further provided and includes a sponge saturated with an antiseptic solution and a protective foil 75 sealing it from the environment.

The apparatus 60 in FIG. 7 has been readied for use. The cap 74 has been removed and the second portion 66 has been detached from the first portion 64 and reattached thereto by the other end. Since the stop 70 is located farther from the other end, the second portion 66 is able to enter the cavity of the first portion 64 more deeply, thereby allowing the needle 68 to pierce through the wall of the storage chamber 62. The spacer 72 may remain attached to the second portion 66 to decrease the length of the needle 68 exposed and available for skin penetration.

Figure 8:
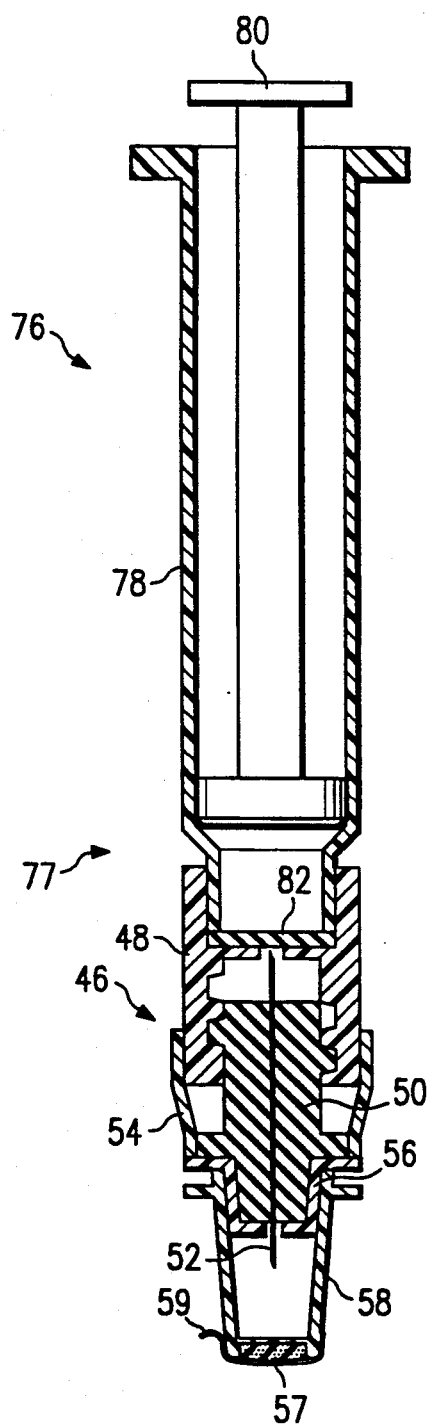
FIG. 8 is a cross-sectional view of a modification of the apparatus of FIG. 4 for use with a intradermal syringe that is also constructed in accordance with the invention.

Referring to FIG. 8, there is illustrated apparatus 75 that is a modification of the apparatus 38 shown in FIG. 4. The apparatus 75 includes a syringe-like element 76 having a hollow body 78 for holding a liquid. The hollow body 78 is further adapted to receive a plunger 80, which is insertable therein at one end and may slidably advance and retreat along the longitudinal direction of the hollow body 78 to decrease and increase the effective volume of the hollow body 78.

At the other end of the hollow body 78 is a stopper element 82 for containing the liquid within the hollow body 78. The stopper element 82 may be made of materials such as rubber or plastic. Further coupled to syringe element 76 is a seat member 46 like that of the apparatus 38 shown in FIGS. 4 and 5. Hereinafter, like numerals refer to like elements in FIGS. 4 and 5 to more clearly describe the structure and function of apparatus 75. Seat member 46 has a first portion 48 coupled to a second portion 50. The first and second portions 48,50 are coupled via a twist-lock mechanism, where the second portion 50 may advance further into the cavity of the first portion 48.

An injecting needle is firmly implanted within the second portion 50 with both ends extending beyond the second portion 50. A casing 54 surrounds the second portion 50 and prevents the second portion from advancing into the first portion 48 prematurely. A spacer 56 is attached to the second portion 50, and coupled thereto is additionally a cap 58 with an antiseptic applicator 57 attached thereto. Applicator 57 includes a sponge and a protective foil 59, such as described in more detail in conjunction with FIG. 1.

Figure 9:
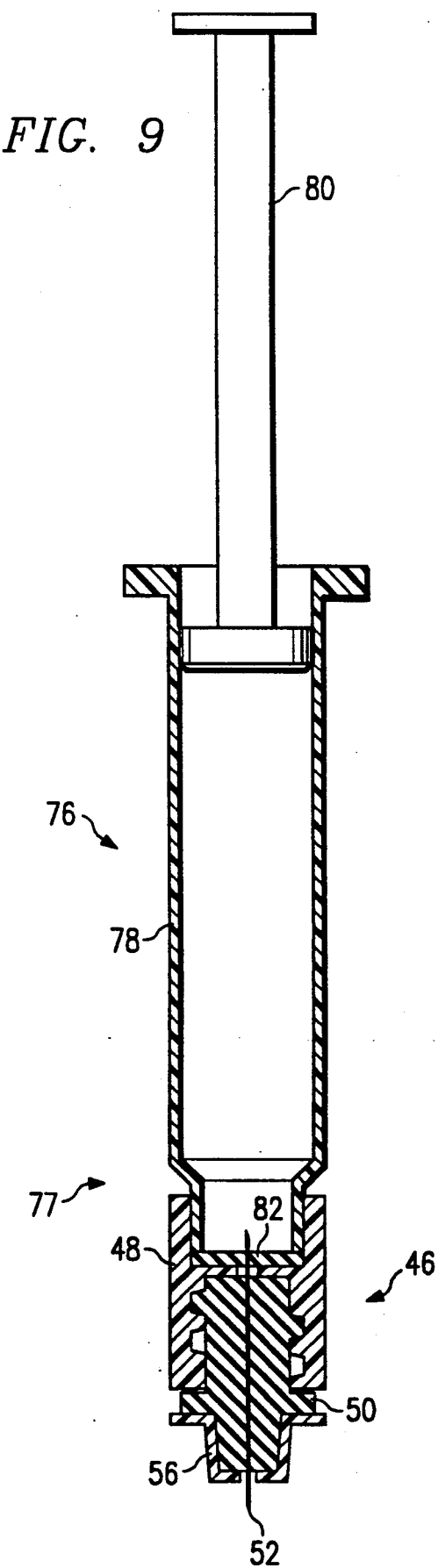
FIG. 9 is a view similar to the view of FIG. 8 showing the apparatus of FIG. 8 as it is ready for use.

Referring to FIG. 9, apparatus 75 has been arranged for immediate use. The casing 54 has been removed so that the second portion 50 may be twisted and advanced further into the cavity of the first portion 48. In doing so, the needle 52 pierces the stopper element 82 and reaches the hollow body 78 of the syringe. Apparatus 75 may now be used like a standard syringe 76 for injecting any liquid to be drawn into the hollow body 78 of the syringe 76 through the needle 52. In addition, the spacer 56 effectively determines the depth of needle penetration into a patient's skin.

Another apparatus 82 that is constructed in accordance with the invention is shown in FIGS. 10 and 11. Apparatus 82 is comprised of a syringe-like element 76 like that of apparatus 75 shown in FIG. 8 and 9, and the seat member 65 shown in FIGS. 6 and 7. Hereinafter, like numerals refer to like elements in FIGS. 6-9 to more clearly illustrate the structure and function of apparatus 82.

Apparatus 82 includes a syringe-like element 76 with a hollow body 78 and a plunger 80. Plunger 80 may slidably advance and retreat within the hollow body 78 to effectively decrease and increase the effective capacity of the hollow body 78. A stopper element 82 forms another liquid proof barrier at the other end of the hollow body 78.

Coupled to the syringe element 76 is a seat member 65. Seat member 65 includes a first portion 64 and a second portion 66. A hollow needle 68 is firmly implanted longitudinally within the second seat member portion 66, and extends substantially beyond the second portion 66 at both ends. The second portion 66 is structurally divided into a short and a long end by a stop 70. The short end may also be constructed to have a substantially larger diameter than the long end. When not in use, as shown in FIG. 10, the short end of the second portion 66 is inserted into a cavity of the first portion 64. Arranged in this fashion, the needle 68 cannot reach and pierce the stopper element 82 of the syringe-like element 76. Additionally, a spacer 72 is arranged between the second portion 66 and the first portion 64, and a cap 74 is detachably coupled to the long end of the second portion 66. Preferably, the cap 74 includes an antiseptic applicator 73 which may consist of a sponge saturated with an antiseptic solution and a protective foil 75.

Referring presently to FIG. 11, the apparatus 82 has been arranged for immediate use. Similar to the apparatus shown in FIGS. 6 and 7, the second portion 66 has been rearranged so that the long end is inserted into the cavity of the first portion 64. Arranged in this manner, the needle 68 is allowed to penetrate the stopper element 82 and reach into the cavity formed by the hollow body 78. Similarly, the spacer 72, still attached to the short end of second portion 66, provides a means for determining the needle penetration depth into the skin.

The use of the various embodiments of the anesthetizing apparatus, as shown in the accompanying drawings, is best described in relation to its application in the field of medicine. More specifically, the various embodiments of the apparatus are used to numb a small area of skin and raise a wheal thereon prior to inserting an I.V. needle and catheter. The administration of the anesthetizing apparatus of the various embodiments is substantially the same. The apparatus may be held substantially perpendicularly to a patient's skin surface over the intended site of I.V. injection. The apparatus is then lowered onto the skin surface until the needle penetrates the skin, where the depth of penetration is determined by the spacer, and the anesthetizing agent is introduced into the skin simultaneously by applying pressure to the storage chamber or plunger. The apparatus is easily operable with one hand and is disposable after use. Accordingly, the pain and suffering usually associated with an I.V. needle is reduced or eliminated, lessening the emotional and physical burden on the patient. The apparatus is compact and self contained. The apparatus requires little preparation prior to use and is disposable after use.

While the embodiments of the invention have been described in detail, it will be understood that many changes and modifications can be made thereto without departing from the spirit or scope of the invention. Other aspects, objects, and advantages of this invention can be obtained from a study of the drawings, the disclosure, and the appended claims.

What is claimed is:

1. A method for anesthetizing skin, comprising the steps of:
   pinching a section of skin to be anesthetized;
   pricking said section of skin with an injector containing an anesthetizing agent;
   limiting the depth of penetration of said injector; and
   forming a skin wheal so that it is readily accessible for intravenous injections or the like.

2. The method, as set forth in claim 1, further comprising the step of applying an antiseptic to the skin prior to said pinching step.

3. The method, as set forth in claim 1, further comprising the step of engaging said injector with a storage chamber containing said anesthetizing agent.

4. The method, as set forth in claim 3, further comprising the step of applying pressure to said storage chamber to force said anesthetizing agent into said injector and skin.

5. The method, as set forth in claim 1, further comprising the step of achieving and maintaining said injector substantially perpendicular to said skin section.

6. A method for anesthetizing skin, comprising the steps of:
   locating a site to be anesthetized;
   penetrating the skin at the site;
   determining the depth of penetration; and
   injecting a solution into the skin to raise a wheal at the site.

7. The method, as set forth in claim 6, wherein said injecting step further comprises the step of engaging an injector with a storage chamber containing said solution.

8. The method, as set forth in claim 7, wherein said injecting step further comprises the step of applying pressure to said storage chamber to force said solution into said injector and skin.

9. A method for painlessly inserting an I.V. needle, comprising the steps of:
   locating a site to be anesthetized;
   penetrating the skin at the site with an injector;
   limiting the depth of penetration of said injector;
   injecting a solution into the skin to raise a wheal at the site; and
   inserting said I.V. needle into said wheal.

10. The method, as set forth in claim 9, further comprising the step of achieving and maintaining said injector substantially perpendicular to said skin section.

11. The method, as set forth in claim 9, further comprising the step of engaging said injector with a storage chamber containing said solution.

12. The method, as set forth in claim 11, wherein said injecting step further comprises the step of applying pressure to said storage chamber to force said solution into said injector and skin.

* * * * *

UNITED STATES PATENT AND TRADEMARK OFFICE
CERTIFICATE OF CORRECTION

PATENT NO. : 5,190,521

DATED : March 2, 1993

INVENTOR(S) : Vance M. Hubbard et al.

It is certified that error appears in the above-identified patent and that said Letters Patent is hereby corrected as shown below:

Column 2, line 16, between "of" and "apparatus" insert -- the --.

Column 2, line 61, between "It" and "preferable" insert -- is --.

Column 4, line 50, delete "58" and insert -- 56 --.

Column 4, line 67 delete "56" and insert -- 58 --.

Column 5, line 2, delete "58" and insert -- 56 --.

Column 5, line 48, delete "75" and insert -- 77 --.

Column 5, line 50, delete "75" and insert -- 77 --.

Column 5, line 66, delete "75" and insert -- 77 --.

Column 6, line 13, delete "75" and insert -- 77 --.

Column 6, line 19, delete "75" and insert -- 77 --.

UNITED STATES PATENT AND TRADEMARK OFFICE
CERTIFICATE OF CORRECTION

PATENT NO. : 5,190,521

DATED : March 2, 1993

INVENTOR(S) : Vance M. Hubbard et al.

It is certified that error appears in the above-identified patent and that said Letters Patent is hereby corrected as shown below:

Column 6, line 24, delete "82" and insert -- 77' --.

Column 6, line 26, delete "82" and insert -- 77' --.

Column 6, line 27, delete "75" and insert -- 77 --.

Column 6, line 31, delete "82" and insert -- 77' --.

Column 6, line 32, delete "82" and insert -- 77' --.

Column 6, line 58, delete "82" and insert -- 77' --.

Signed and Sealed this

Twelfth Day of April, 1994

BRUCE LEHMAN

*Commissioner of Patents and Trademarks*

*Attest:*

*Attesting Officer*